(12) United States Patent
Jackson, III et al.

(10) Patent No.: US 11,877,759 B2
(45) Date of Patent: Jan. 23, 2024

(54) SYNDESMOTIC RECONSTRUCTION GUIDE ASSEMBLY

(71) Applicant: CROSSROADS EXTREMITY SYSTEMS, LLC, Memphis, TN (US)

(72) Inventors: James Benjamin Jackson, III, Irmo, SC (US); Michael Chad Hollis, Collierville, TN (US); Daniel Ryan Sayger, Hernando, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 438 days.

(21) Appl. No.: 17/320,701

(22) Filed: May 14, 2021

(65) Prior Publication Data

US 2021/0353309 A1 Nov. 18, 2021

Related U.S. Application Data

(60) Provisional application No. 63/025,197, filed on May 15, 2020.

(51) Int. Cl.
| | |
|---|---|
| *A61B 17/17* | (2006.01) |
| *A61B 17/02* | (2006.01) |
| *A61B 17/68* | (2006.01) |
| *A61B 90/00* | (2016.01) |

(52) U.S. Cl.
CPC ...... *A61B 17/1775* (2016.11); *A61B 17/1714* (2013.01); *A61B 17/1796* (2013.01); *A61B 90/39* (2016.02); *A61B 2090/3966* (2016.02)

(58) Field of Classification Search
CPC ....................... A61B 17/1714; A61B 17/1775
See application file for complete search history.

(56) References Cited

U.S. PATENT DOCUMENTS

| | | | | |
|---|---|---|---|---|
| 2004/0254585 | A1* | 12/2004 | Whittaker | A61B 17/1714 606/104 |
| 2009/0234356 | A1* | 9/2009 | Bickley | A61B 17/68 606/59 |
| 2013/0030442 | A1* | 1/2013 | Pilgeram | A61B 17/1764 606/96 |
| 2016/0089159 | A1* | 3/2016 | Ardito | A61B 17/1714 606/96 |
| 2019/0059917 | A1* | 2/2019 | Saltzman | A61B 17/1682 |

* cited by examiner

*Primary Examiner* — Christian A Sevilla
(74) *Attorney, Agent, or Firm* — BakerHostetler

(57) ABSTRACT

A syndesmotic reconstruction guide assembly is disclosed. The syndesmotic reconstruction guide assembly includes a medial arm, a medial foot, and a lateral arm. The medial foot is rotatably connected to the medial arm with at least one degree of freedom. The lateral arm is slidably connected to the medial arm at an end opposite the medial foot. The lateral arm includes a lateral foot. The medial foot and the lateral foot are adapted to clamp bones of a syndesmotic joint therebetween.

19 Claims, 13 Drawing Sheets

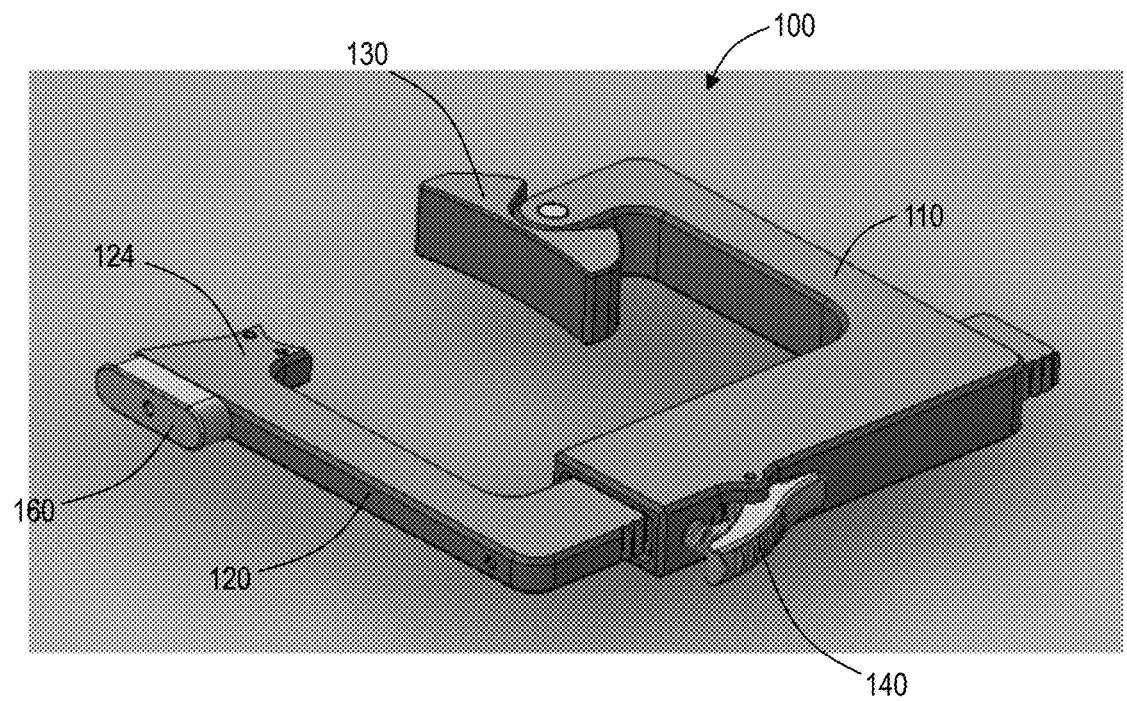
FIG. 5
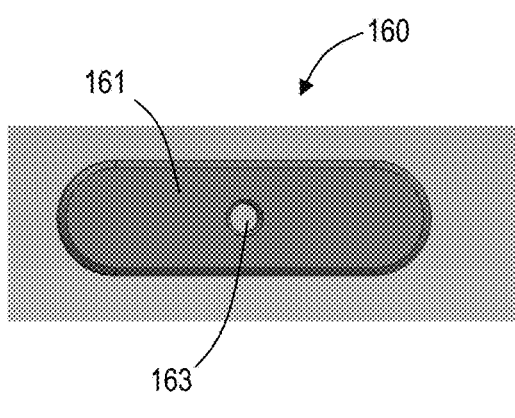 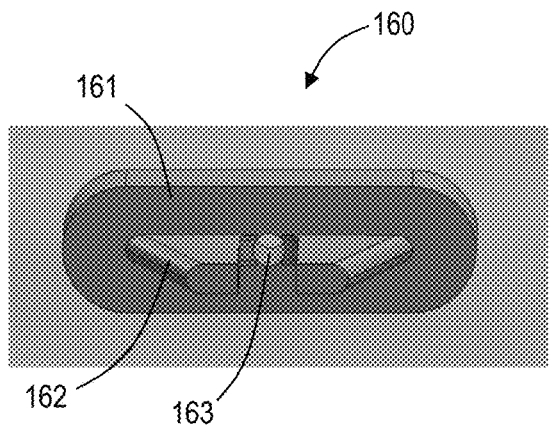
FIG. 6   FIG. 7

SYNDESMOTIC RECONSTRUCTION GUIDE ASSEMBLY

CROSS-REFERENCE TO RELATED APPLICATION

The present disclosure claims the benefit of priority of U.S. Provisional Patent Application 63/025,197, filed on May 15, 2020, and entitled "SYNDESMOTIC RECONSTRUCTION GUIDE AND AID," the contents of which are incorporated in full by reference herein.

FIELD OF THE DISCLOSURE

The present disclosure generally relates to the medical field. More particularly, the present disclosure relates to a syndesmotic reconstruction guide assembly.

BACKGROUND OF THE DISCLOSURE

Ligaments interconnect bones of the skeletal system and are involved with the stabilization and kinematics of skeletal joints. Various injuries may occur that result in compromised ligament function. Such injuries include, for example, partial and complete tears and avulsion of the bone where a ligament attaches to a bone. Ligament injuries occur throughout the skeletal system.

By way of example, the human ankle is a complex junction of multiple bones and soft tissues. The ankle includes joints between the tibia, fibula, and talus. The joint between the tibia and fibula is a syndesmosis or slightly movable joint in which the bones are joined together by connective tissue. The syndesmosis between the tibia and fibula includes the anterior inferior tibiofibular ligament (AITFL), the posterior inferior tibiofibular ligament (PITFL), and the interosseous ligament (IOL). The syndesmosis ligaments are often injured in high ankle sprains. Other injury prone ligaments of the ankle joint include, among others, the anterior talofibular ligament (ATFL), the posterior talofibular ligament (PTFL) and the deltoid ligament complex including superficial and deep deltoid ligaments. Other injuries, such as fractures to the tibia, fibula, and talus, at or near the ankle joint can also be problematic.

Syndesmotic reconstruction can be used to help these injuries heal by securing the bones of the syndesmotic joint, such as the tibia and the fibula, together with a screw or suture to reduce the pressure on the injured ligament or fractured portion of a bone so that the injury can heal.

The above-described background relating to syndesmosis joints, the injuries thereof, and medical procedures therefore is merely intended to provide a contextual overview of some current issues related to syndesmosis joints and is not intended to be exhaustive. Other contextual information may become apparent to those of ordinary skill in the art upon review of the following description of exemplary embodiments.

BRIEF SUMMARY OF THE DISCLOSURE

The present disclosure generally provides a syndesmotic reconstruction guide assembly for use during syndesmotic reconstruction. Ordinarily, a surgeon will form anchor holes in the bones of a syndesmotic joint and anchor the bones with anchoring implants positioned within the anchor holes simply by eyeballing where to form the anchor holes. Such a procedure relies heavily on the skill of the surgeon. By performing the syndesmotic reconstruction with the reconstruction guide assembly disclosed herein, the precision of the procedure can be improved as the surgeon is guided thereby in forming the anchor holes.

In some of the embodiments disclosed herein, the syndesmotic reconstruction guide assembly includes a medial foot with at least one degree of freedom relative to the medial arm that it is connected thereto, radio-opaque alignment guides, and guide inserts attachable to a lateral arm of the syndesmotic reconstruction guide assembly. Due to the degree of freedom of the medial foot, the medial foot can be rotated and positioned to better contact a bone of the syndesmotic joint to better secure the syndesmotic reconstruction guide assembly to the bones at or adjacent to the syndesmotic joint. The radio-opaque alignment guides provide visual guides that can be used to aide in the alignment of the syndesmotic reconstruction guide assembly relative to the syndesmotic joint. As the guide inserts are attachable (and removable) from the syndesmotic reconstruction guide assembly, multiple guide inserts with guide holes in varying positions and orientations can be used to guide the formation of multiple sets of anchor holes in the bones at different orientations. The surgeon can select the guide inserts based on the desired positions of the desired anchor holes.

In one illustrative embodiment of the present disclosure, a syndesmotic reconstruction guide assembly is disclosed. The syndesmotic reconstruction guide assembly includes a medial arm, a medial foot, and a lateral arm. The medial foot is rotatably connected to the medial arm with at least one degree of freedom. The lateral arm is slidably connected to the medial arm at an end opposite the medial foot. The lateral arm includes a lateral foot. The medial foot and the lateral foot are adapted to clamp bones of a syndesmotic joint therebetween.

In some embodiments, the medial foot includes a medial contact surface and the lateral foot includes a lateral contact surface, and wherein each of the medial foot and the lateral foot include a curvature adapted to match that of a bone received thereby.

In some embodiments, the lateral arm includes a guide slot formed therein extending towards a lateral contact surface of the lateral foot, the syndesmotic reconstruction guide assembly further comprising a guide insert including one or more mating protrusions adapted to be received in the guide slot and a guide hole adapted to guide tooling to a predetermined position relative to a syndesmotic joint. Optionally, the guide hole is offset relative to the guide slot.

In some embodiments, the syndesmotic reconstruction guide assembly includes one or more alignment guides that are radio-opaque and adapted for aligning the syndesmotic reconstruction guide assembly relative to a syndesmotic joint. Optionally, the one or more alignment guides includes an alignment wire embedded in radiolucent material and the alignment wire is adapted to align parallel to an angle of an ankle mortise of the syndesmotic joint.

In some embodiments, the one or more alignment guides includes alignment pins positioned on each side of a lateral guide hole, within the lateral arm and a pin positioned at or adjacent to the medial foot, and the alignment pins are aligned with the pin centered therebetween while looking down a sightline of a lateral guide hole of the lateral foot.

In another illustrative embodiment of the present disclosure, a method for performing syndesmotic reconstruction is disclosed. The method includes securing the syndesmotic reconstruction guide assembly to bones of the syndesmotic joint by positioning a medial foot of the syndesmotic reconstruction guide assembly, with at least one degree of freedom relative to a medial arm of the syndesmotic reconstruction guide assembly, against a first bone of the syndesmotic joint and positioning a lateral foot of a lateral arm of the syndesmotic reconstruction guide assembly, mated with the medial arm in a slidable relationship, against a second bone of the syndesmotic joint. The method also includes aligning the syndesmotic reconstruction guide assembly relative to the syndesmotic joint. The method further includes forming one or more sets of anchor holes in the bones of the syndesmotic joint with tooling guided by the syndesmotic reconstruction guide assembly. The method yet further includes anchoring the bones together by positioning an anchoring implant within each of the one or more sets of anchor holes.

In some embodiments, aligning the syndesmotic reconstruction guide assembly relative to the syndesmotic joint includes utilizing radio-opaque alignment guides to align the syndesmotic reconstruction guide assembly relative to the syndesmotic joint. Optionally, the radio-opaque alignment guides include an alignment wire that is aligned parallel to an angle of the ankle mortise of the syndesmotic joint. Optionally, X-rays are taken from different angles to ensure that the alignment guides are properly aligned relative to the syndesmotic joint. Optionally, alignment pins are positioned on each side of a lateral guide hole, within the lateral arm, which are aligned with a pin positioned at or adjacent to the medial foot. Optionally, an X-ray is taken down the sightline of the lateral guide hole and the two alignment pins are aligned with the pin centered therebetween.

In some embodiments, forming the one or more sets of the anchor holes in the bones of the syndesmotic joint with the tooling includes attaching a guide insert to the lateral arm and using an insert guide hole therein to guide the tooling, and wherein the guide insert is selected based on a desired position and angle of a set of anchor holes.

In a further illustrative embodiment of the present disclosure, a clamp for guiding syndesmotic reconstruction is disclosed. The clamp includes a medial arm, a medial foot, a lateral arm, and alignment guides. The medial foot adjoins the medial arm. The lateral arm is slidably connected to the medial arm at an end opposite the medial foot. The lateral arm includes a lateral foot. The medial foot and the lateral foot are adapted to clamp bones of a syndesmotic joint therebetween. The alignment guides include a radio-opaque material at least partially embedded in one of the medial arm and the lateral arm.

In some embodiments, the alignment guides include an alignment wire that is aligned parallel to an angle of the ankle mortise of the syndesmotic joint.

In some embodiments, the lateral arm includes a lateral guide hole extending to a lateral contact surface of the lateral foot, the one or more alignment guides includes alignment pins positioned on each side of the lateral guide hole and a pin positioned at or adjacent to the medial foot, and the alignment pins are aligned with the pin centered therebetween while looking down a sightline of a lateral guide hole of the lateral foot to align the clamp relative to the syndesmotic joint.

In some embodiments, the lateral arm includes a guide slot formed therein extending towards a lateral contact surface of the lateral foot and a lateral guide hole extending from the guide slot to the lateral contact surface, and wherein the guide slot is adapted to mate with a guide insert that is adapted to guide tooling to a predetermined position relative to the syndesmotic joint.

In some embodiments, the medial foot includes a medial contact surface and the lateral foot includes a lateral contact surface, and wherein each of the medial foot and the lateral foot include a curvature adapted to match that of a bone received thereby.

In some embodiments, the medial foot rotatably connected to the medial arm with at least one degree of freedom.

BRIEF DESCRIPTION OF THE DRAWINGS

The present disclosure is illustrated and described herein with reference to the various drawings, in which like reference numbers are used to denote like system components/method steps, as appropriate, and in which:

FIG. 5 is a perspective view of the syndesmotic reconstruction guide assembly of FIG. 1 including an illustrative embodiment with a guide insert;

FIG. 6 is a front perspective view of the guide insert of FIG. 5;

FIG. 7 is back perspective view of the guide insert of FIG. 5;

DETAILED DESCRIPTION OF THE DISCLOSURE

Again, the present disclosure generally provides a syndesmotic reconstruction guide assembly for use during syndesmotic reconstruction. Ordinarily, a surgeon will form anchor holes in the bones of a syndesmotic joint and anchor the bones with anchoring implants positioned within the anchor holes simply by eyeballing where to form the anchor holes. Such a procedure relies heavily on the skill of the surgeon. By performing the syndesmotic reconstruction with the reconstruction guide assembly disclosed herein, the precision of the procedure can be improved as the surgeon is guided thereby in forming the anchor holes.

As will be discussed in greater detail below, in some of the embodiments disclosed herein, the syndesmotic reconstruction guide assembly includes a medial foot with at least one degree of freedom relative to the medial arm that it is connected thereto, radio-opaque alignment guides, and guide inserts attachable to a lateral arm of the syndesmotic reconstruction guide assembly. Due to the degree of freedom of the medial foot, the medial foot can be rotated and positioned to better contact a bone of the syndesmotic joint to better secure the syndesmotic reconstruction guide assembly to the bones at or adjacent to the syndesmotic joint. The radio-opaque alignment guides provide visual guides that can be used to aide in the alignment of the syndesmotic reconstruction guide assembly relative to the syndesmotic joint. As the guide inserts are attachable (and removable) from the syndesmotic reconstruction guide assembly, multiple guide inserts with guide holes in varying positions and orientations can be used to guide the formation of multiple sets of anchor holes in the bones at different orientations. The surgeon can select the guide inserts based on the desired positions of the desired anchor holes.

Figure 1:
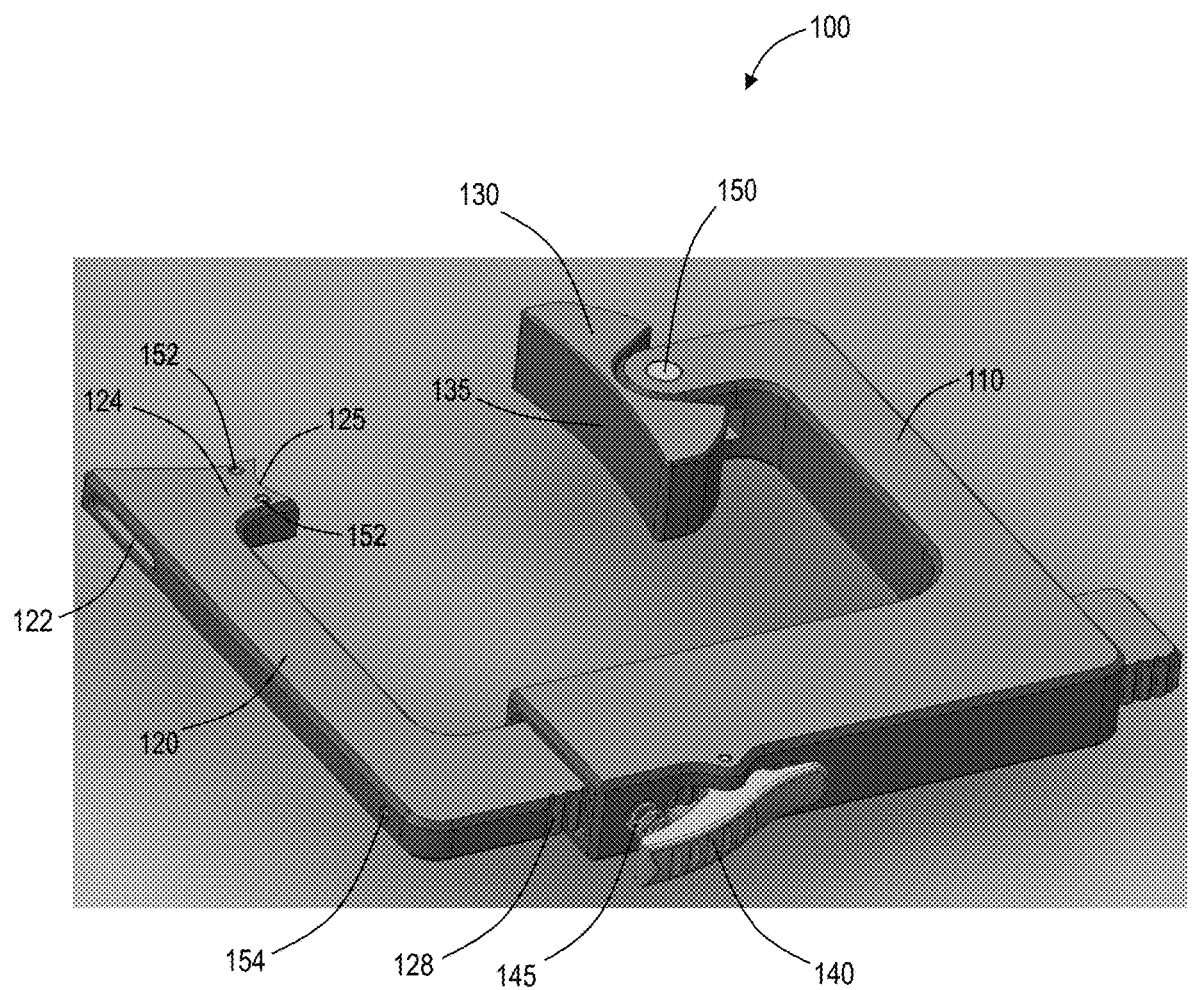
FIG. 1 is a perspective view of an illustrative embodiment of a syndesmotic reconstruction guide assembly of the present disclosure.
Figure 2:
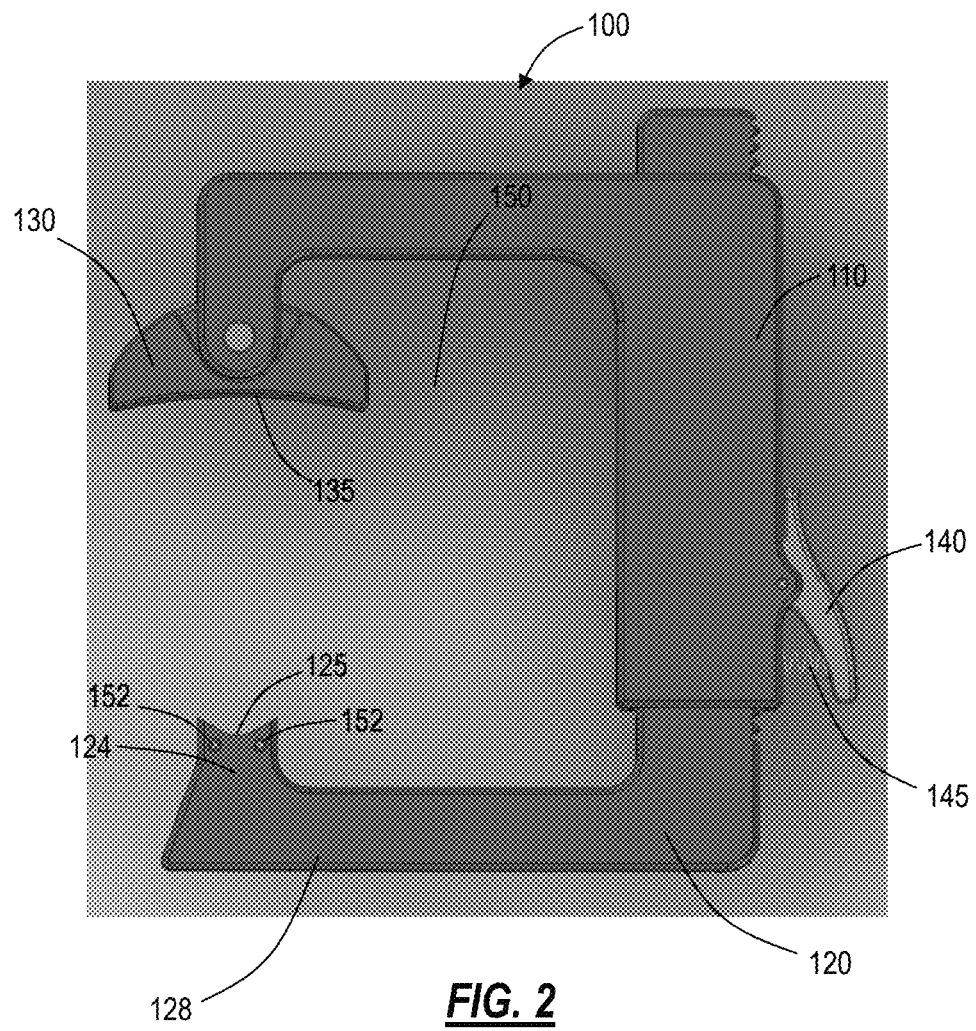
FIG. 2 is a top perspective view of the syndesmotic reconstruction guide assembly of FIG. 1.
Figure 3:
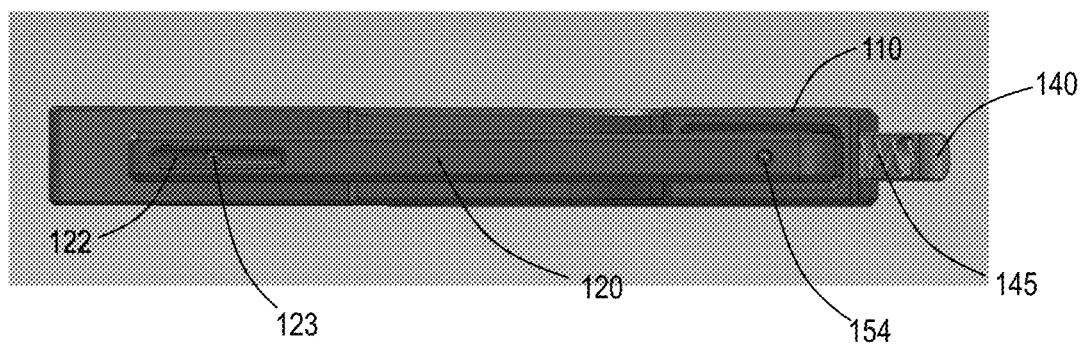
FIG. 3 is a side perspective view of the syndesmotic reconstruction guide assembly of FIG. 1.

FIG. 1 is a perspective view of an illustrative embodiment of a syndesmotic reconstruction guide assembly 100 of the present disclosure. FIG. 2 is a top perspective view of the syndesmotic reconstruction guide assembly 100 of FIG. 1. FIG. 3 is a side perspective view of the syndesmotic reconstruction guide assembly 100 of FIG. 1. Referring to FIGS. 1-3, in embodiments, the syndesmotic reconstruction guide assembly 100 includes a medial arm 110, a lateral arm 120, and a medial foot 130. In embodiments, the medial arm 110 and the lateral arm 120 are adapted to mate in a slidable relationship forming a clamp, such as a C-clamp and include a mechanism for securing the lateral arm 120 relative to the medial arm 110.

In the embodiment illustrated, the medial arm 110 and the lateral arm 120 are in a ratcheting relationship, such that opposing sides of the medial arm 110 and the lateral arm 120 can be brought closer together while the ratcheting relationship prevents the separation thereof. In the embodiment illustrated, the lateral arm 120 is received in the medial arm 110, in a telescoping arrangement, and includes ratcheting teeth 128, and the mechanism is a pawl 140, secured to the medial arm 110, that engages the ratcheting teeth 128. In other embodiments, the medial arm 110 is received in the lateral arm 120, in a telescoping arrangement, and the medial arm 110 includes the ratcheting teeth that engage the pawl 140, which is secured to the lateral arm 120. In embodiments, a spring 145 biases the pawl 140 into engagement with the ratcheting teeth 128. Other configurations and mechanisms for securing the medial arm 110 to the lateral arm 120 are also contemplated.

The medial foot 130 is rotatably connected to an end of the medial arm 110 that is opposite the connection of the medial arm 110 to the lateral arm 120. The rotatable connection between the medial foot 130 and the medial arm 110 includes at least one degree of freedom. In the embodiment illustrated, the medial foot 130 is connected to the medial arm 110 via a pin 150. However, other connections are also contemplated, such as a ball and socket joint. The medial foot 130 includes a medial contact surface 135 adapted to contact a bone (this contact can be indirect since skin and other tissue may be present between the medial contact surface 135 and the bone), such as a tibia 10 (refer to FIG. 12). In embodiments, the medial contact surface 135 includes a curvature adapted to receive the bone, such as a curvature matching that of the bone. In some embodiments, the medial contact surface 135 includes protrusions, such as tines, adapted to grip the bone/tissue that it contacts to secure the syndesmotic reconstruction guide assembly 100 in place.

The lateral arm 120 includes a lateral foot 124. The lateral foot 124 includes a lateral contact surface 125 that faces towards the medial contact face 135. The lateral contact surface 125 is adapted to contact a bone (this contact can be indirect since skin and other tissue may be present between the medial contact surface 135 and the bone, such as being in loading contact and directly adjacent to the bone), such as a fibula 20 (refer to FIG. 12). In embodiments, the lateral contact surface 125 includes a curvature adapted to receive the bone, such as a curvature matching that of the bone. In some embodiments, the lateral contact surface 125 includes protrusions, such as tines, adapted to grip the bone/tissue that it contacts to secure the syndesmotic reconstruction guide assembly 100 in place. In the embodiment illustrated, the lateral foot 124 extends towards the medial foot 130. The medial foot 130 and the lateral foot 124 are adapted to clamp bones of the syndesmotic joint therebetween.

In some embodiments, the lateral arm 120 also includes a guide slot 122 extending toward the lateral contact surface 125. In some embodiments, the guide slot 122 tapers, narrowing as the guide slot 122 gets closer to the lateral contact surface 125. In some embodiments, the lateral arm 120 also includes a lateral guide hole 123 extending from the guide slot 122 to the lateral contact surface 125. In some embodiments, the guide slot 122 and the lateral guide hole 123 are formed in the lateral arm 120 and are at least partially formed in the lateral foot 124. As will be discussed in greater detail below, in embodiments, the lateral guide slot 122 is adapted to receive guide inserts 160 (refer to FIGS. 5-10).

Figure 4:
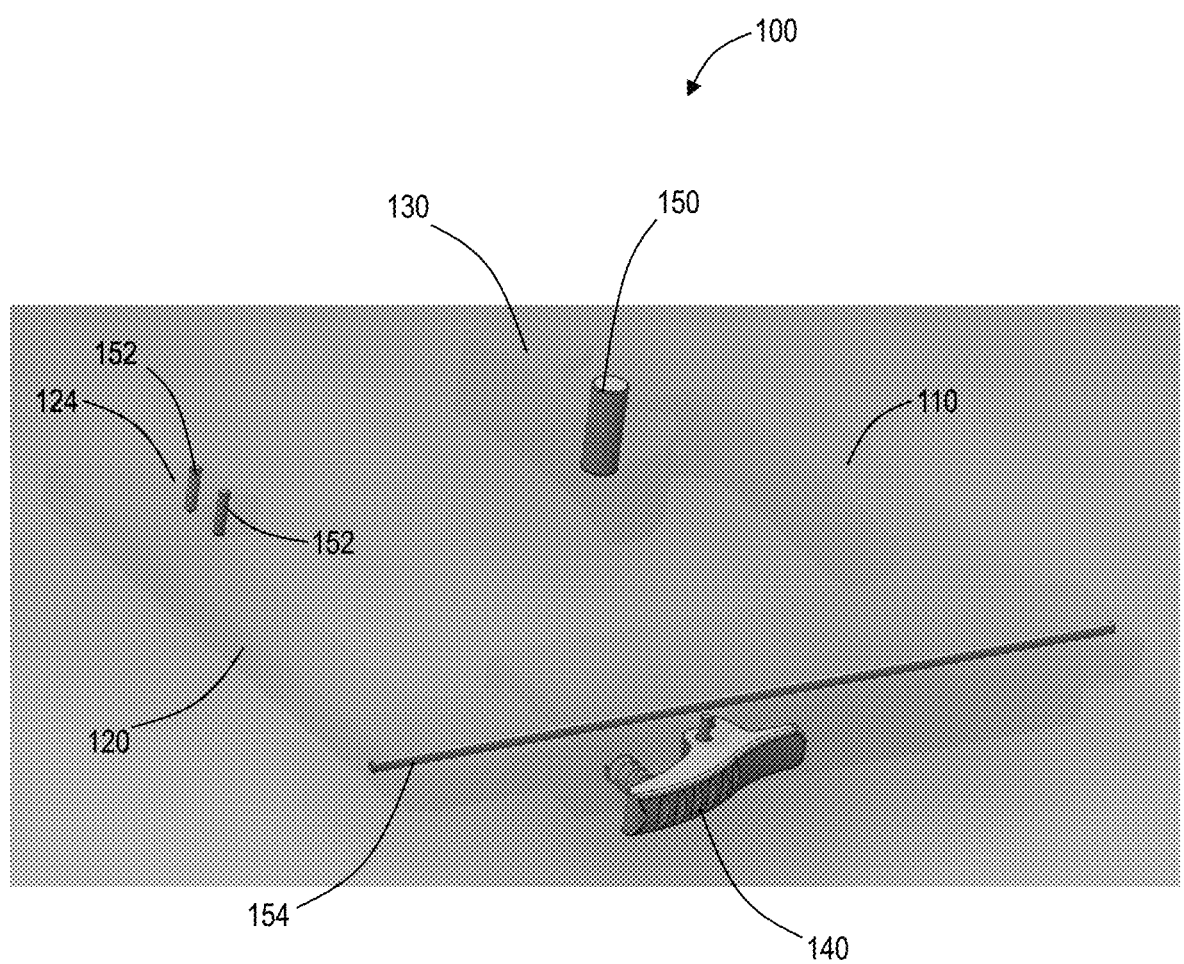
FIG. 4 is a perspective view of the syndesmotic reconstruction guide assembly of FIG. 1 highlighting alignment guides thereof.

In embodiments, the syndesmotic reconstruction guide assembly 100 includes one or more alignment guides. In the embodiment illustrated, the alignment guides include the pin 150, alignment pins 152, and an alignment wire 154. FIG. 4 is a perspective view of the syndesmotic reconstruction guide assembly 100 of FIG. 1 highlighting alignment guides thereof. Referring to FIG. 4, the alignment guides are radio-opaque and are not transparent to X-rays or other forms of radiation. In the embodiment illustrated, the pin 150 and the alignment wire 154 are at least partially embedded in the medial arm 110, which is formed of a radiolucent material, and the alignment pins 152 are at least partially embedded in the lateral arm 120, which is also formed of a radiolucent material.

In the embodiment illustrated, the pin 150 is adapted to both form the joint between the medial arm 110 and the medial foot 130 and act as an alignment guide. In other embodiments, the pin 150 is adapted to function as an alignment guide and is a separate structure to the feature forming the joint between the medial arm 110 and the medial foot 130.

In the embodiment illustrated, the alignment wire 154 extends parallel to the leg of the lateral arm 120 within which it is embedded. In other embodiments, the alignment wire 154 is embedded in the medial arm 110. In further embodiments, the alignment wire 154 is embedded in radiolucent material that attaches to one of the medial arm 110 and the lateral arm 120, such that the alignment wire 154 is offset from the medial arm 110 and the lateral arm 120. In embodiments, the amount of offset is based on a desired position of the clamp formed by the medial arm 110 and the lateral arm 120 relative to syndesmotic joint, and in some embodiments, relative to the ankle mortise.

In the embodiment illustrated, the alignment pins 152 extend parallel to the pin 150 and are positioned on opposing sides of the lateral guide hole 123, adjacent and offset from the lateral contact surface 125. As will be discussed in greater detail below, the alignment guides are positioned and adapted to help align the syndesmotic reconstruction guide assembly 100 relative to the syndesmotic joint in at least one of the axial, coronal, and sagittal planes, and in particular are adapted to align the syndesmotic reconstruction guide assembly 100 relative to the ankle mortise.

FIG. 5 is a perspective view of the syndesmotic reconstruction guide assembly 100 of FIG. 1 including an illustrative embodiment with a guide insert 160. FIG. 6 is a front perspective view of the guide insert 160 of FIG. 5. FIG. 7 is back perspective view of the guide insert 160 of FIG. 5. Referring now to FIGS. 5-7, in embodiments, the syndesmotic reconstruction guide assembly 100 includes one or more guide inserts 160. In embodiments, the guide inserts 160 are adapted to guide the formation of anchor holes in the bones and to guide anchor implants into position within the anchor holes. Different guide inserts 160 can be used for different tools, such as K-wires and drills, and different anchor implants, such as screws and sutures.

In the embodiment illustrated in FIGS. 5-7, the guide insert 160 includes a body 161, an insert guide hole 163, and one or more mating protrusions 162. The insert guide hole 163 extends through the body 161 and is adapted to align with the lateral guide hole 123. The size and orientation of the insert guide hole 163 is based on the type of tools, implants, and desired positioning thereof, which can be selected by the surgeon performing the syndesmotic reconstruction. The insert guide hole 163 is adapted to guide tooling to a predetermined position relative to the syndesmotic joint.

The one or more mating protrusions 162 extend from the body 161 without obstructing the insert guide hole 163. The one or more mating protrusions 162 are adapted to be received in the guide slot 122. In some embodiments, the one or more mating protrusions 162 are tapered, to match the taper of the guide slot 122, and in some embodiments, the one or more mating protrusions 162 are adapted to form an interference fit with the guide slot 122 upon insertion therein.

Figure 8:
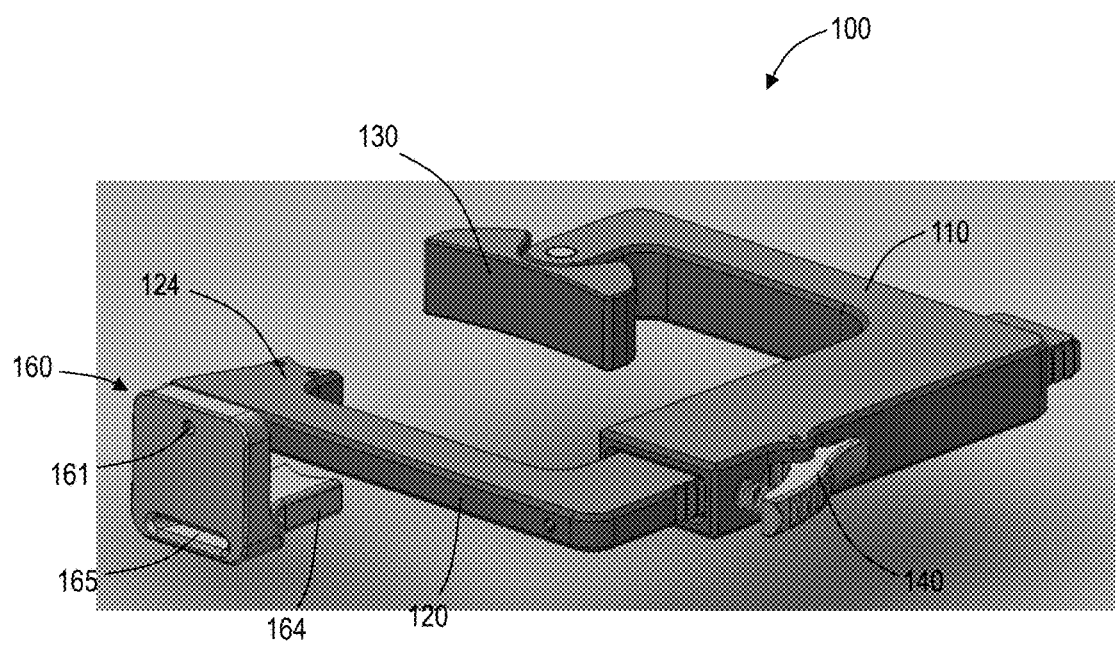
FIG. 8 is a perspective view of the syndesmotic reconstruction guide assembly of FIG. 1 including another illustrative embodiment with a guide insert.
Figure 9:
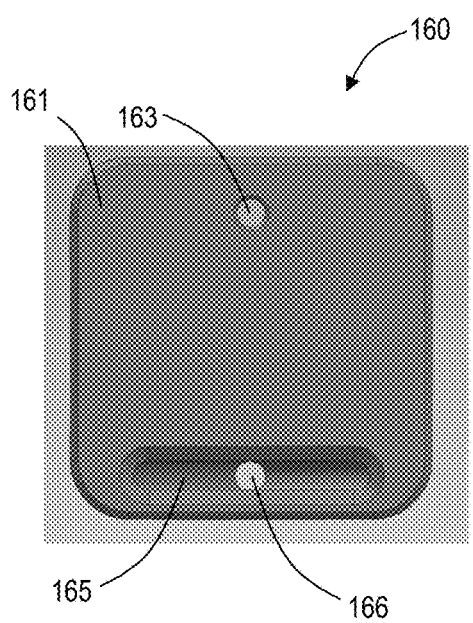
FIG. 9 is a front perspective view of the guide insert of FIG. 8.
Figure 10:
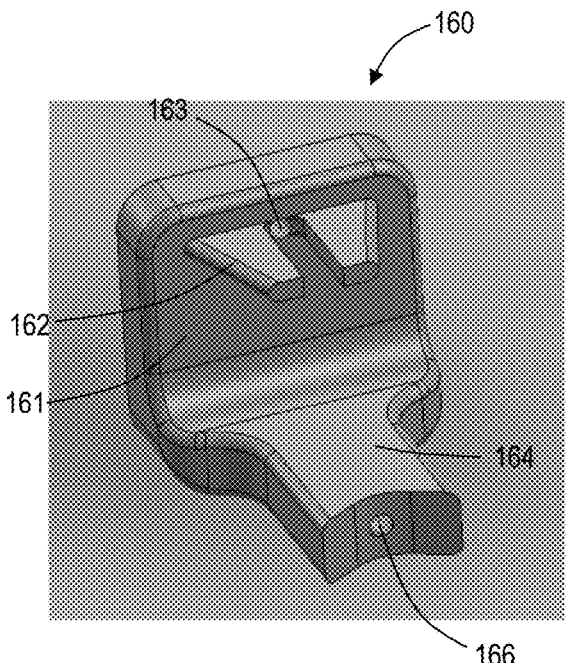
FIG. 10 is back perspective view of the guide insert of FIG. 8.

FIG. 8 is a perspective view of the syndesmotic reconstruction guide assembly 100 of FIG. 1 including another illustrative embodiment with a guide insert 160. FIG. 9 is a front perspective view of the guide insert 160 of FIG. 8. FIG. 10 is back perspective view of the guide insert 160 of FIG. 8. Referring to FIGS. 8-10, in embodiments, the guide insert 160 includes the body 161 and the one or more mating protrusions 162 along with an offset guide body 164 and an offset guide hole 166. The offset guide body 164 is offset from the one or more mating protrusions 162. The offset guide hole 166 is formed in the offset guide body 164 and is adapted to guide one or more of a tool and an implant therethrough. In embodiments, the offset guide body 164 is adapted to guide the tool/implant to a desired position and orientation. In some embodiments, the guide insert 160 includes an offset guide slot 165 formed in the offset guide body 164 and aligned with the offset guide hole 166. The offset guide slot 165 is adapted to receive another guide insert 160 allowing the offset position of the offset guide slot 165 to be utilized with different tools and implants depending on the guide insert 160 mated therein allowing for preparation of the bones for implant anchors in multiple planes.

Figure 11:
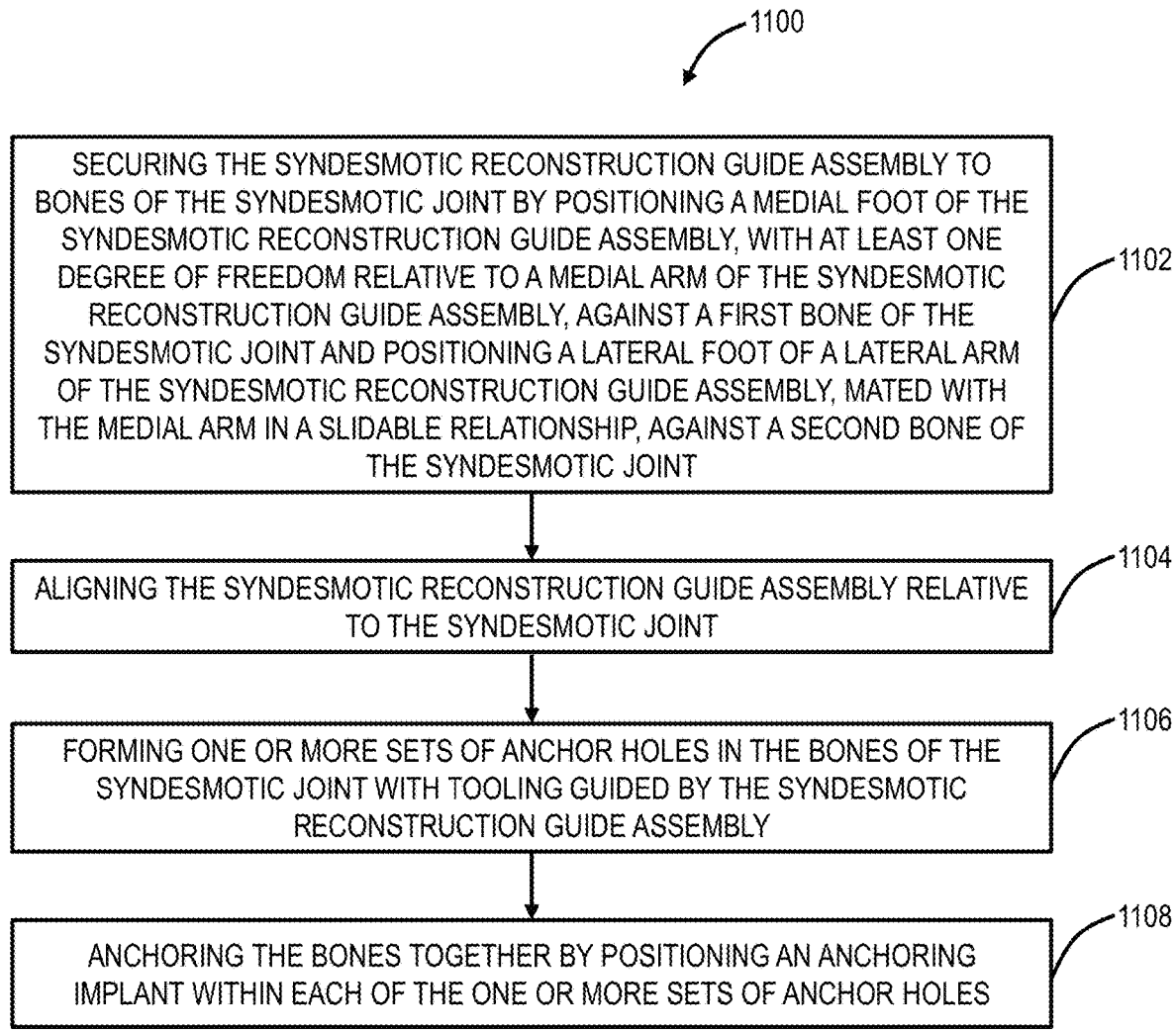
FIG. 11 is a flowchart of a method for performing syndesmotic reconstruction.
Figure 12:
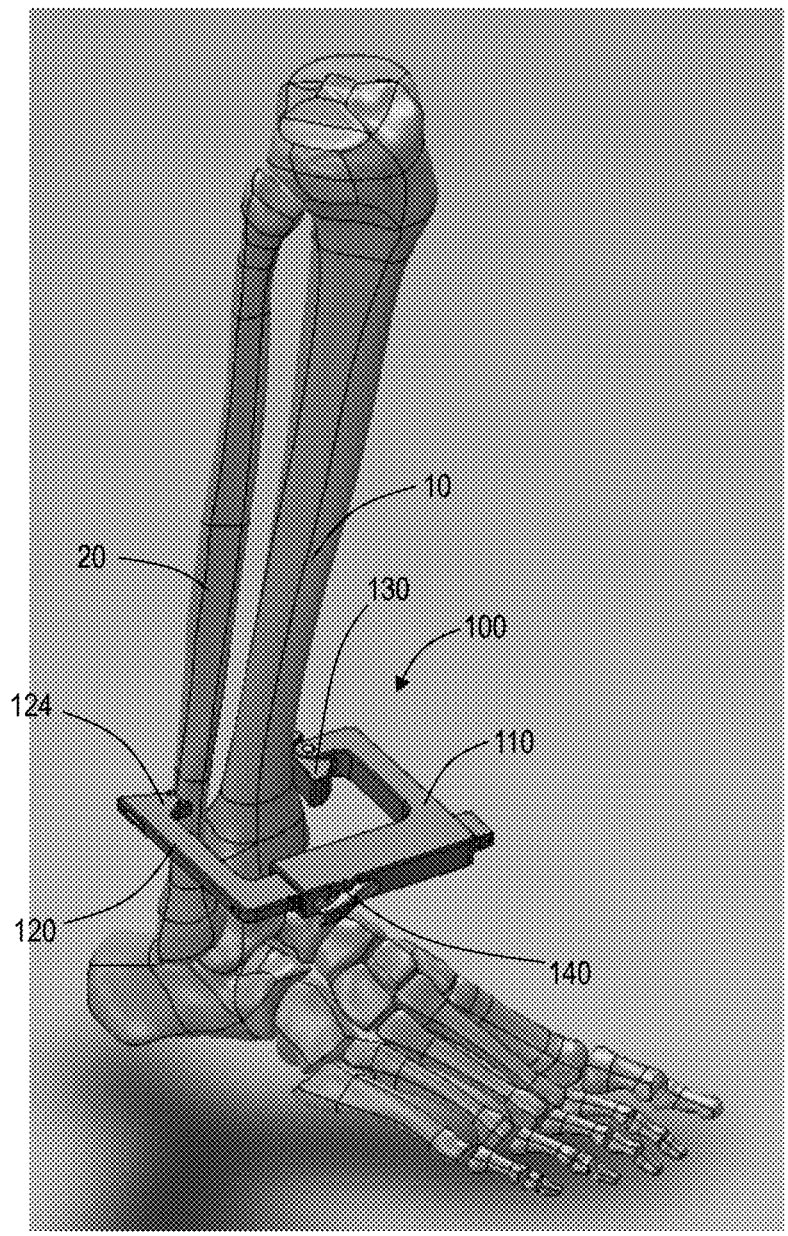
FIG. 12 is a perspective view of the syndesmotic reconstruction guide assembly of FIG. 1 secured to bones of a syndesmotic joint.
Figure 13:
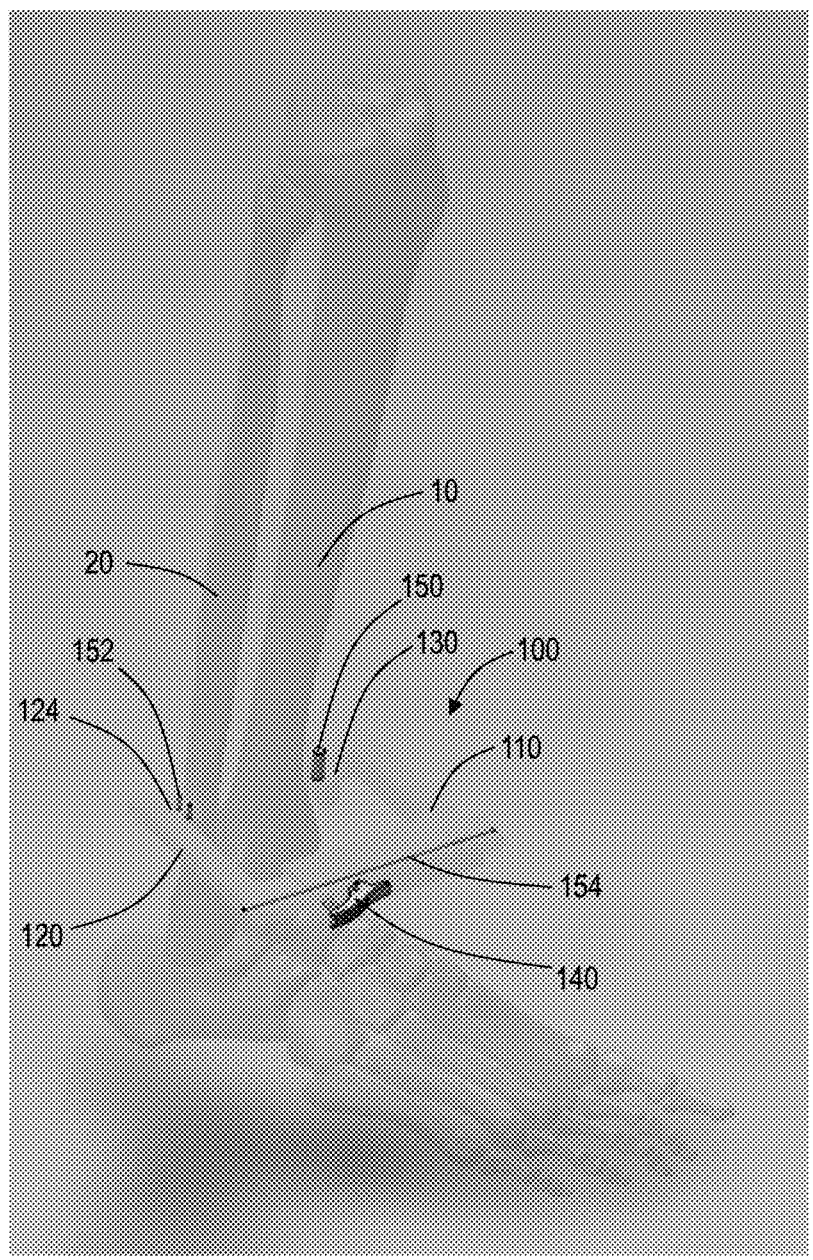
FIG. 13 is a perspective view of the syndesmotic reconstruction guide assembly of FIG. 1 secured to bones of a syndesmotic joint highlighting the alignment guides thereof.
Figure 14:
FIG. 14 is a side perspective view of the ankle mortise highlighting and angle of the ankle mortise.
Figure 15:
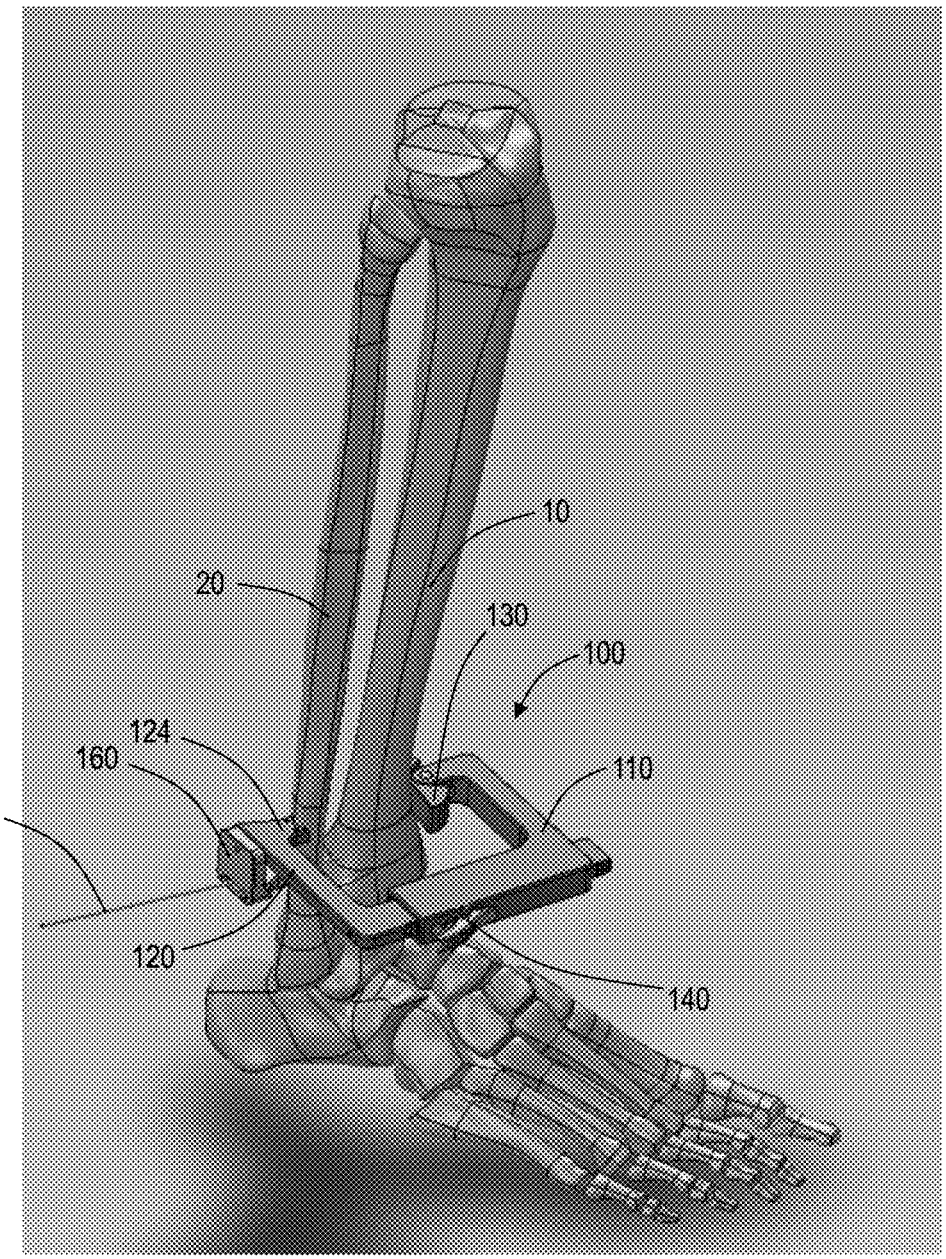
FIG. 15 is a perspective view of the syndesmotic reconstruction guide assembly of FIG. 1 secured to bones of a syndesmotic joint highlighting the formation of anchor holes through the bones.
Figure 16:
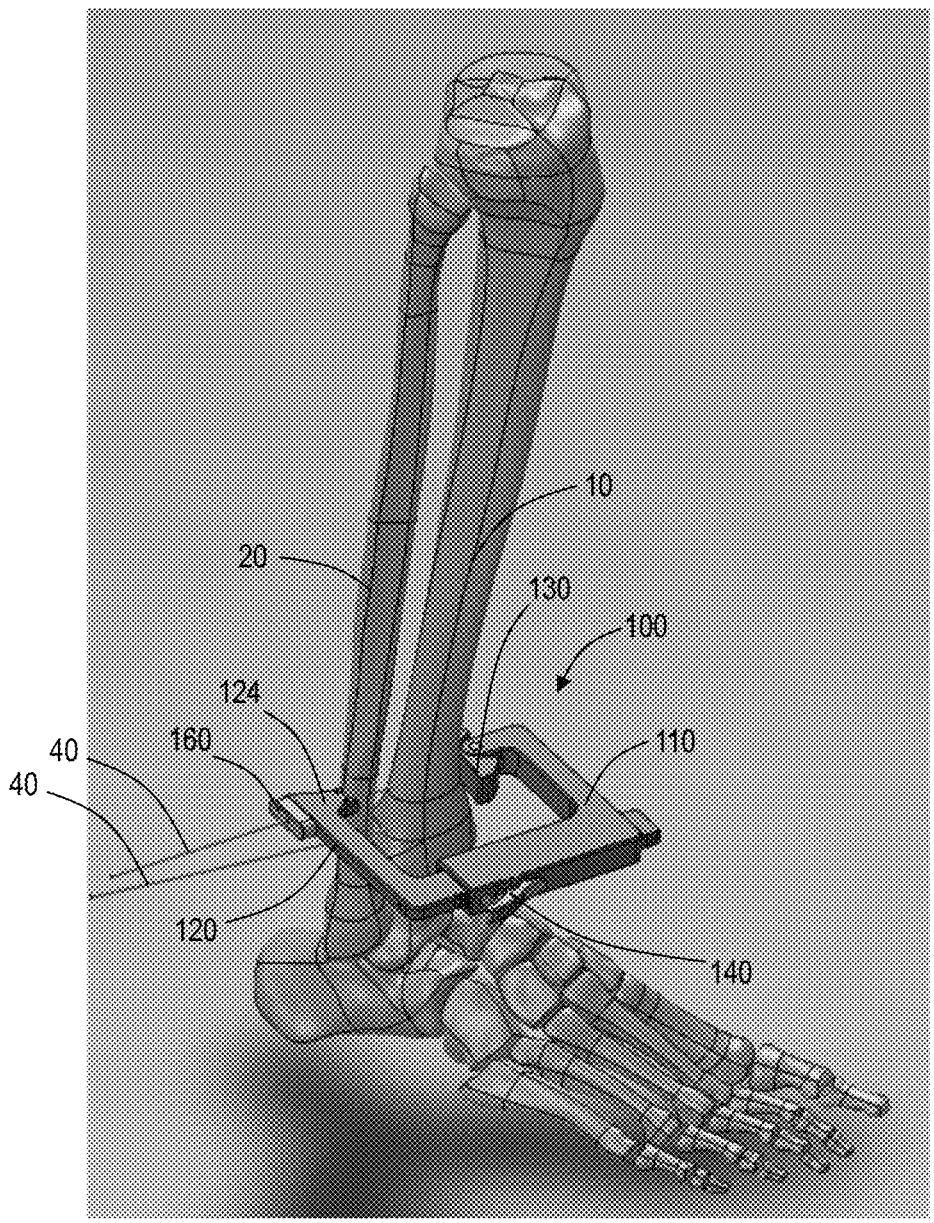
FIG. 16 is a perspective view of the syndesmotic reconstruction guide assembly of FIG. 1 secured to bones of a syndesmotic joint highlighting the formation of further anchor holes through the bones.
Figure 17:
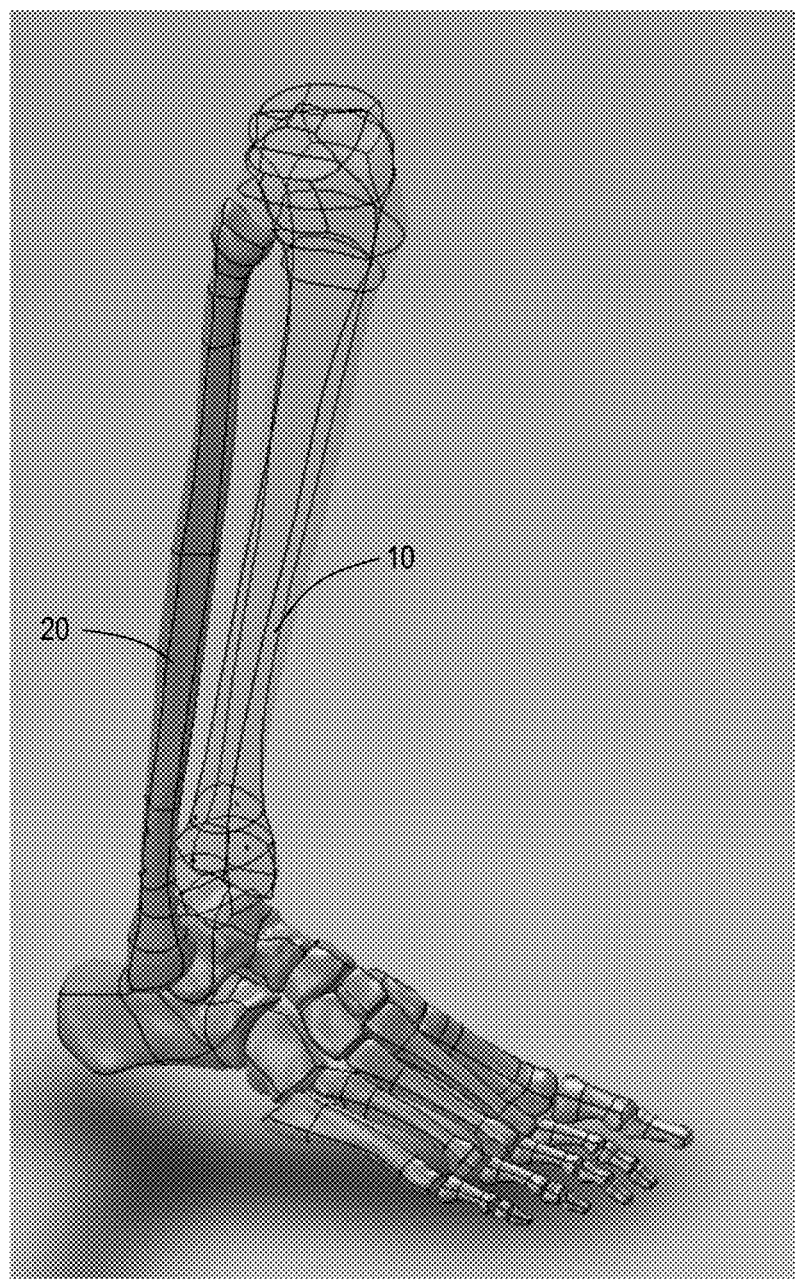
FIG. 17 is a perspective view of the syndesmotic joint highlighting the anchor holes in the bones.
Figure 18:
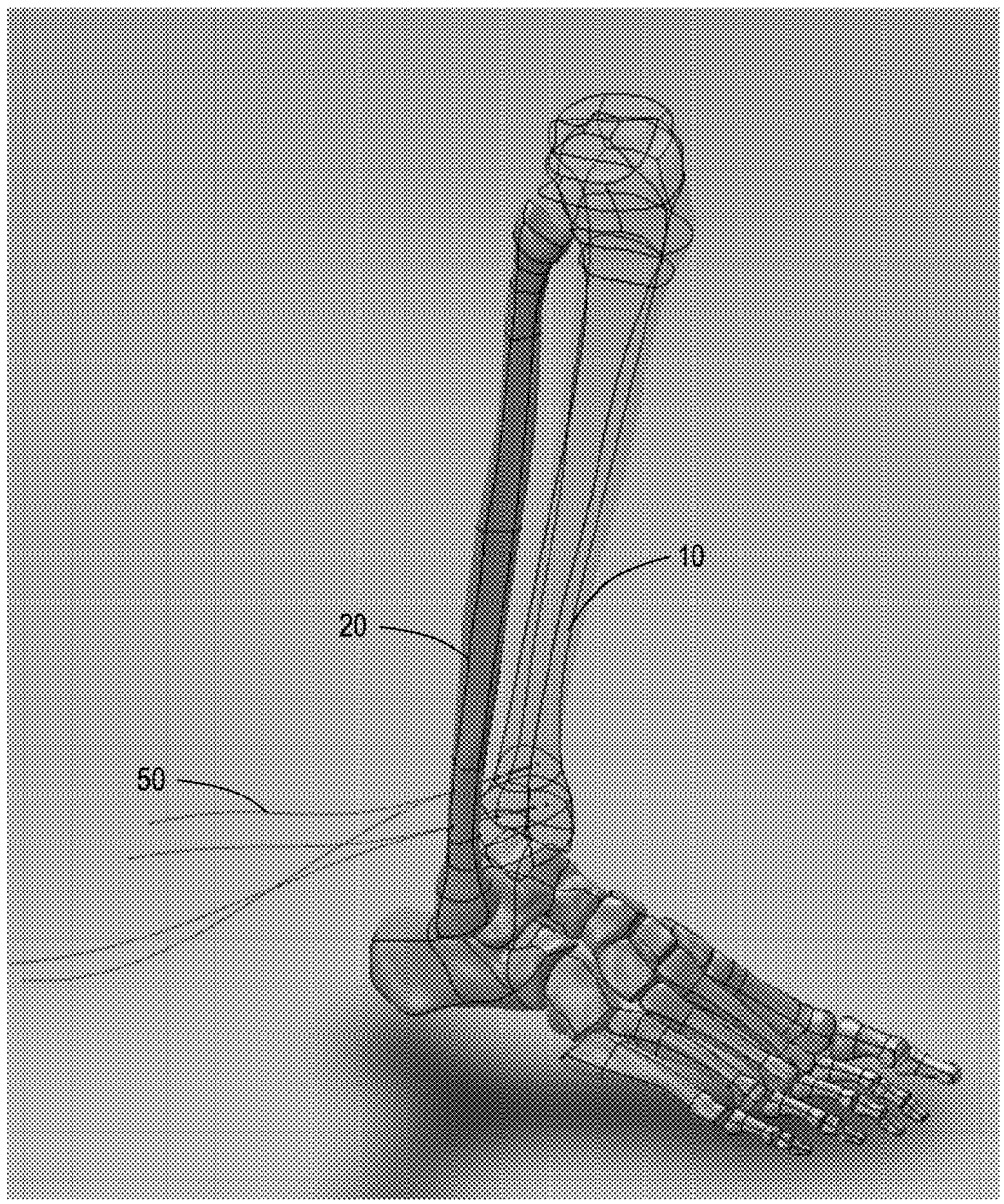
FIG. 18 is a perspective view of the syndesmotic joint highlighting anchoring implants inserted into the anchor holes.

FIG. 11 is a flowchart of a method 1100 for performing syndesmotic reconstruction. FIG. 12 is a perspective view of the syndesmotic reconstruction guide assembly 100 of FIG. 1 secured to bones of a syndesmotic joint. FIG. 13 is a perspective view of the syndesmotic reconstruction guide assembly 100 of FIG. 1 secured to bones of a syndesmotic joint highlighting the alignment guides thereof. FIG. 14 is a side perspective view of the ankle mortise highlighting and angle of the ankle mortise. FIG. 15 is a perspective view of the syndesmotic reconstruction guide assembly 100 of FIG. 1 secured to bones of a syndesmotic joint highlighting the formation of anchor holes through the bones. FIG. 16 is a perspective view of the syndesmotic reconstruction guide assembly 100 of FIG. 1 secured to bones of a syndesmotic joint highlighting the formation of further anchor holes through the bones. FIG. 17 is a perspective view of the syndesmotic joint highlighting the anchor holes in the bones. FIG. 18 is a perspective view of the syndesmotic joint highlighting anchoring implants 30 inserted into the anchor holes.

Referring to FIGS. 11-18, the method 1100 includes securing the syndesmotic reconstruction guide assembly 100 to bones of the syndesmotic joint by positioning a medial foot 130 of the syndesmotic reconstruction guide assembly 100, with at least one degree of freedom relative to a medial arm 110 of the syndesmotic reconstruction guide assembly 100, against a first bone of the syndesmotic joint and positioning a lateral foot 124 of a lateral arm 120 of the syndesmotic reconstruction guide assembly 100, mated with the medial arm 110 in a slidable relationship, against a second bone of the syndesmotic joint at step 1102. Referring to FIG. 12, in embodiments, the syndesmotic joint is the joint between the tibia 10 and the fibula 20, and the medial foot 130 is secured against the tibia 10 and the lateral foot is secured against the fibula 20.

The method 1100 also includes aligning the syndesmotic reconstruction guide assembly 100 relative to the syndesmotic joint at step 1104. Referring to FIG. 13, in embodiments, step 1104 includes utilizing radio-opaque alignment guides to align the syndesmotic reconstruction guide assembly 100 relative to the syndesmotic joint. In embodiments, X-rays are taken from different angles to ensure that the alignment guides are properly aligned. In some embodiments, an alignment wire 154 is aligned parallel to the angle of the ankle mortise. The angle of the ankle mortise is illustrated in FIG. 14. In some embodiments, the alignment wire 154 is embedded in an attachment that positions the alignment wire 154 at offset to the clamp formed by the medial arm 110 and the lateral arm 120 where the offset is adapted to overlap with the ankle mortise while the syndesmotic reconstruction guide assembly 100 is properly aligned with the syndesmotic joint.

In some embodiments, alignment pins 152 are positioned on each side of a lateral guide hole 123, within the lateral arm 120, which are aligned with a pin 150 positioned at or adjacent to the medial foot 130. In embodiments, an X-ray is taken down the sightline of the lateral guide hole 123 and the two alignment pins 152 are aligned with the pin 150 centered therebetween similar to the alignment of a gunsight. With the use of the alignment guides, the syndesmotic reconstruction guide assembly 100, and in particular, the clamp formed by the medial arm 110 and the lateral arm 120, can be aligned in each of the axial, coronal, and sagittal planes relative to the syndesmotic joint and the ankle mortise. In some embodiments, the alignment guides include a circular element, such as a hollow cylinder and a torus, positioned at one of the lateral side and the medial side, such as around the lateral guide hole 123 in the lateral arm 120, and a spherical element positioned in the opposite of the lateral side and the medial side, such as in the medial foot 130 or medial arm 110. In these embodiments, alignment is performed by aligning the circular and spherical elements, such as by aligning the centers thereof.

The method 1100 further includes forming one or more sets of anchor holes in the bones of the syndesmotic joint with tooling 40 guided by the syndesmotic reconstruction guide assembly 100 at step 1106. In embodiments, the tooling 40 is one of a K-wire, a drill, and the like. In embodiments, step 1106 includes attaching a guide insert 160 to the lateral arm 120 and using an insert guide hole 163 therein to guide the tooling. In some embodiments, as can be seen in FIGS. 15-17, multiple guide inserts 160 are used to form multiple sets of anchor holes in the bones. The guide insert 160 selected can be based on the desired position and angle of the anchor holes.

The method yet further includes anchoring the bones together by positioning an anchoring implant 50 within each of the one or more sets of anchor holes at step 1108 (refer to FIG. 18). In embodiments, the anchoring implants 50 are one of a screw, sutures, suture buttons, and the like.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A syndesmotic reconstruction guide assembly, comprising:
a medial arm;
a medial foot rotatably connected to the medial arm with at least one degree of freedom; and
a lateral arm slidably connected to the medial arm at an end opposite the medial foot, the lateral arm including a lateral foot, the medial foot and the lateral foot adapted to clamp bones of a syndesmotic joint therebetween.

2. The syndesmotic reconstruction guide assembly of claim 1, wherein the medial foot includes a medial contact surface and the lateral foot includes a lateral contact surface, and wherein each of the medial foot and the lateral foot include a curvature adapted to match that of a bone received thereby.

3. The syndesmotic reconstruction guide assembly of claim 1, wherein the lateral foot comprises a lateral contact surface, and the lateral arm includes a guide slot formed therein extending towards the lateral contact surface of the lateral foot, the syndesmotic reconstruction guide assembly further comprising a guide insert including one or more mating protrusions adapted to be received in the guide slot and a guide hole adapted to guide tooling to a predetermined position relative to a syndesmotic joint.

4. The syndesmotic reconstruction guide assembly of claim 1, further comprising one or more alignment guides that are radio-opaque and adapted for aligning the syndesmotic reconstruction guide assembly relative to a syndesmotic joint.

5. The syndesmotic reconstruction guide assembly of claim 4, wherein the one or more alignment guides includes an alignment wire embedded in radiolucent material, the alignment wire being adapted to align parallel to an angle of an ankle mortise of the syndesmotic joint.

6. The syndesmotic reconstruction guide assembly of claim 1, wherein the lateral arm comprises a lateral guide hole formed within the lateral arm, and the one or more alignment guides includes alignment pins positioned on each side of the lateral guide hole, and the medial arm comprises a pin positioned at or adjacent to the medial foot, and wherein the alignment pins are aligned with the pin, and the pin is adapted to be centered between the alignment pins while looking down a sightline of the lateral guide hole.

7. A method for performing syndesmotic reconstruction using a syndesmotic reconstruction guide assembly comprising a medial arm comprising a medial foot and a lateral arm comprising a lateral foot, comprising:
securing the syndesmotic reconstruction guide assembly to bones of a syndesmotic joint by positioning the medial foot of the medial arm of the syndesmotic reconstruction guide assembly, the medial foot having at least one degree of freedom relative to the medial arm of the syndesmotic reconstruction guide assembly, against a first bone of the syndesmotic joint and positioning the lateral foot of the lateral arm of the syndesmotic reconstruction guide assembly, the lateral arm being mated with the medial arm in a slidable relationship, against a second bone of the syndesmotic joint;
aligning the syndesmotic reconstruction guide assembly relative to the syndesmotic joint;
forming one or more sets of anchor holes in the bones of the syndesmotic joint with tooling guided by the syndesmotic reconstruction guide assembly; and
anchoring the bones together by positioning an anchoring implant within each of the one or more sets of anchor holes.

8. The method of claim 1, wherein aligning the syndesmotic reconstruction guide assembly relative to the syndesmotic joint includes utilizing radio-opaque alignment guides to align the syndesmotic reconstruction guide assembly relative to the syndesmotic joint.

9. The method of claim 8, wherein the radio-opaque alignment guides include an alignment wire that is adapted to be aligned parallel to an angle of the ankle mortise of the syndesmotic joint.

10. The method of claim 8, further comprising taking X-rays from different angles to ensure that the alignment guides are properly aligned relative to the syndesmotic joint.

11. The method of claim 8, wherein the medial arm comprises a pin positioned at or adjacent the medial foot, the lateral arm comprises a lateral guide hole within the lateral arm, and the lateral arm comprises alignment pins positioned on each side of the lateral guide hole, the alignment pins being aligned with the pin.

12. The method of claim 11, further comprising taking an X-ray down a sightline of the lateral guide hole, and the two alignment pins are adapted to be aligned with the pin centered therebetween.

13. The method of claim 7, wherein forming the one or more sets of the anchor holes in the bones of the syndesmotic joint with the tooling includes attaching a guide insert to the lateral arm and using an insert guide hole therein to guide the tooling, and wherein the guide insert is selected based on a desired position and angle of a set of anchor holes.

14. A clamp for guiding syndesmotic reconstruction, the clamp comprising:
a medial arm;
a medial foot adjoining the medial arm;
a lateral arm slidably connected to the medial arm at an end opposite the medial foot, the lateral arm including a lateral foot, the medial foot and the lateral foot adapted to clamp bones of a syndesmotic joint therebetween; and
one or more alignment guides comprising a radio-opaque material at least partially embedded in one of the medial arm and the lateral arm.

15. The clamp of claim 14, wherein the one or more alignment guides include an alignment wire that is adapted to be aligned parallel to an angle of the ankle mortise of the syndesmotic joint.

16. The clamp of claim 14, wherein the lateral foot comprises a lateral contact surface, the lateral arm includes a lateral guide hole extending to the lateral contact surface of the lateral foot, wherein the one or more alignment guides includes alignment pins positioned on each side of the lateral guide hole and the medial arm comprises a pin positioned at or adjacent to the medial foot, and wherein the alignment pins are adapted to be aligned with the pin centered therebetween while looking down a sightline of the lateral guide hole to align the clamp relative to the syndesmotic joint.

17. The clamp of claim 14, wherein the lateral foot comprises a lateral contact surface, and the lateral arm includes a guide slot formed therein extending towards the lateral contact surface of the lateral foot and a lateral guide hole extending from the guide slot to the lateral contact surface, and wherein the guide slot is adapted to mate with a guide insert that is adapted to guide tooling to a predetermined position relative to the syndesmotic joint.

18. The clamp of claim 14, wherein the medial foot includes a medial contact surface and the lateral foot includes a lateral contact surface, and wherein each of the medial foot and the lateral foot include a curvature adapted to match that of a bone received thereby.

19. The clamp of claim 14, wherein the medial foot is rotatably connected to the medial arm with at least one degree of freedom.

* * * * *